(12) United States Patent
Weber (10) Patent No.: US 7,329,267 B2
(45) Date of Patent: Feb. 12, 2008

(54) MEDICAL CUTTING DEVICES AND METHODS OF USE

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 661 days.

(21) Appl. No.: 10/328,366

(22) Filed: Dec. 23, 2002

(65) Prior Publication Data

US 2004/0122457 A1 Jun. 24, 2004

(51) Int. Cl.
*A61B 17/22* (2006.01)
*A61B 17/32* (2006.01)
*A61B 17/24* (2006.01)
*A61B 10/00* (2006.01)

(52) U.S. Cl. ............... 606/159; 606/170; 606/180; 606/113; 600/564

(58) Field of Classification Search ............... 606/159, 606/198, 113, 170, 180; 600/564, 471
See application file for complete search history.

(56) References Cited

U.S. PATENT DOCUMENTS

| | | | |
|---|---|---|---|
| 4,696,667 A | 9/1987 | Masch | |
| 4,728,319 A | 3/1988 | Masch | |
| 4,840,176 A | 6/1989 | Ohno | |
| 5,030,201 A | 7/1991 | Palestrant | |
| 5,047,040 A | 9/1991 | Simpson et al. | |
| 5,078,722 A | 1/1992 | Stevens | |
| 5,152,773 A | 10/1992 | Redha | |
| 5,226,909 A | 7/1993 | Evans et al. | |
| 5,250,059 A | 10/1993 | Andreas et al. | |
| 5,287,858 A | 2/1994 | Hammerslag et al. | |
| 5,372,601 A | 12/1994 | Lary | |
| 5,417,703 A | 5/1995 | Brown et al. | |
| 5,441,510 A | 8/1995 | Simpson et al. | |
| 5,507,760 A | 4/1996 | Wynne et al. | |
| 5,507,761 A | 4/1996 | Duer | |
| 5,522,825 A | 6/1996 | Kropf et al. | |
| 5,569,277 A * | 10/1996 | Evans et al. | 606/159 |
| 5,628,761 A | 5/1997 | Rizik | |
| 5,643,296 A | 7/1997 | Hundertmark et al. | |
| 5,713,913 A | 2/1998 | Lary et al. | |
| 5,843,103 A | 12/1998 | Wulfman | |
| 5,895,402 A | 4/1999 | Hundertmark et al. | |
| 6,102,938 A * | 8/2000 | Evans et al. | 623/1.35 |
| 6,165,187 A * | 12/2000 | Reger | 606/159 |
| 6,258,108 B1 * | 7/2001 | Lary | 606/159 |
| 6,331,166 B1 | 12/2001 | Burbank et al. | |
| 6,451,036 B1 | 9/2002 | Heitzmann et al. | |
| 6,508,773 B2 * | 1/2003 | Burbank et al. | 600/567 |

FOREIGN PATENT DOCUMENTS

WO   WO 01/60262   8/2001

* cited by examiner

*Primary Examiner*—(Jackie) Tan-Uyen Ho
*Assistant Examiner*—Melissa Ryckman
(74) *Attorney, Agent, or Firm*—Crompton, Seager & Tufte, LLC (57) ABSTRACT

Intravascular cutting device that does not require an inflatable balloon for blade deployment. A cutting wire can be reversibly moved between a retracted, non-cutting position in which the cutting wire does not contact tissue and an extended, cutting position in which the cutting wire does contact tissue.

10 Claims, 7 Drawing Sheets

MEDICAL CUTTING DEVICES AND METHODS OF USE

TECHNICAL FIELD

The invention relates generally to medical devices and more particularly to medical devices that are adapted for use in vivo to remove vascular obstructions.

BACKGROUND

Medical cutting or ablating devices for use within a patient's anatomy are known. For example, intravascular devices can employ cutting balloons for excising obstructions within a patient's vasculature. A cutting balloon typically is an inflatable balloon having one or more cutting blades that can be positioned in parallel with a long axis of the balloon. The balloon has a deflated position in which cutting blades are retracted from a cutting position and an inflated position in which the cutting blades are extended into a cutting position.

Existing cutting balloons have distinct disadvantages. For example, the steel blades typically employed require the application of significant force to successfully cut away the lesions present in the vascular system. Because the cutting or outward force is applied by inflating the balloon, this places limits on how small the balloon can be.

A substantial need remains for an alternative in vivo cutting device.

SUMMARY

The invention provides design, material, structural and manufacturing alternatives for cutting devices adapted for use within a patient's anatomy. In some embodiments, the invention is directed to a cutting device that does not require an inflatable balloon for blade deployment and thus can optionally be made smaller than conventional cutting balloons. A cutting wire can be reversibly moved between a retracted, non-cutting position in which the cutting wire does not contact tissue and an extended, cutting position in which the cutting wire does contact tissue.

Accordingly, one example embodiment is found in a cutting device that has a first securement member and a second securement member that can be positioned away from the first securement member. A cutting wire has a first end that can be attached to the first securement member and a second end that can be attached to the second securement member. An activation wire can be-attached to the first securement member.

Another example embodiment is found in a cutting device that has a housing with a longitudinal slot and a sliding securement member that can be positioned within the housing. A stationary securement member can be positioned away from the sliding securement member. A cutting wire has a distal end that can be attached to the sliding securement member and a proximal end that can be attached to the stationary securement member. An activation wire can be attached to the sliding securement member such that manipulating the activation wire moves the sliding securement member towards the stationary securement member and causes the cutting wire to extend outwards through the longitudinal slot.

Another example embodiment is found in a cutting device that has a housing with a longitudinal slot and a cutting unit. The cutting unit includes a distal securement member, a proximal securement member and a cutting wire that can be attached at either end to the distal securement member and the proximal securement member. An activation wire can be attached to the distal securement member. The cutting device also includes a positioning securement member that can be proximal of the cutting unit and that can be secured to the housing. Biasing means can be positioned between the cutting unit and the positioning securement member. The cutting unit can be biased to a non-cutting configuration.

Another example embodiment is found in a method of excising material or tissue from the anatomy of a patient, such as a lesion within a vascular system. A cutting device is provided that includes a first securement member, a second securement member that can be positioned proximal of the first securement member and a cutting wire that can be attached at either end to the first securement member and the second securement member. An activation wire that can be attached to the first securement member can be pulled to move the first securement member proximally towards the second securement member, thereby moving the cutting wire into a cutting position. The cutting device can be rotated to cut out the lesion.

Although discussed with specific reference to use within the vasculature of a patient, for example to excise a lesion, medical cutting devices and methods of use in accordance with the invention can be adapted and configured for use in other parts of the anatomy. For example, devices and methods in accordance with the invention can be adapted and configured for use within the digestive system, the respiratory system, or other parts of the anatomy of a patient.

DETAILED DESCRIPTION

The present invention is directed to a cutting device, for example an intravascular cutting device, that does not require an inflatable balloon for blade deployment and that employs a cutting wire that can be reversibly moved between a non-cutting position and cutting position.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout several views. The detailed description and drawings are intended to illustrate but not limit the claimed invention.

As illustrated in the Figures, a cutting device in accordance with an embodiment of the present invention, such as an intravascular cutting device 10, can include a cutting unit 12 that includes a first securement member 14, a second securement member 16 and a cutting wire 18 that is positioned between the first securement member 14 and the second securement member 16 and is attached at either end to the first securement member 14 and the second securement member 16. The cutting unit 12 can include one, two, three, four or more cutting wires 18 that can be equally or non-equally spaced around each of the first securement member 14 and the second securement member 16.

As illustrated, the cutting unit 12 has four cutting wires 18, each radially spaced 90 degrees apart. In other embodiments, the cutting unit 12 can include three cutting wires 18 radially spaced 120 degrees apart. The cutting unit 12 can include a single cutting wire 18, or the cutting unit 12 can include two cutting wires 18 radially spaced 180 degrees apart. Alternatively, the cutting unit 12 can include one or more cutting wires 18 that are not equally spaced. For lesions that are present on only one side of a blood vessel, there can be advantages to having a cutting unit 12 with cutting wires 18 crowded to one side or the other of the cutting unit 12.

The cutting wires 18 can be made with materials such as metals, metal alloys, polymers, metal-polymer composites, or other suitable materials, and the like. Some examples of some suitable materials can include stainless steels (e.g. 304v stainless steel or 316L stainless steel), nickel-titanium alloys (e.g., nitinol such as super elastic or linear elastic nitinol), nickel-chromium alloys, nickel-chromium-iron alloys, cobalt alloys, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

A cutting wire 18 includes a cutting blade 20 that is attached to the cutting wire 18. If the blade 20 is not integral with the wire 18, the blade 20 is attached or connected to the wire 20 using any of a broad variety of suitable attachment techniques, depending upon the types of materials being joined. For example, the blade can be attached to the wire using joining techniques such as adhesive bonding, welding, soldering, brazing, crimping, friction fitting, thermal bonding, and the like.

The cutting blade 20 can be made of any suitable material that would provide the desired cutting characteristics. In some embodiments, the cutting blade 20 can be a diamond blade 20 that enables nearly force-free cutting. In some embodiments, the diamond blade 20 can have a cutting edge that is only several atoms wide and a radius of only 3 nanometers. As illustrated, each cutting wire 18 has a single blade 20 secured at or near a midpoint of the cutting wire 18. While not illustrated, each cutting wire 18 can have a plurality of blades 20 spaced out along the length of the cutting wire 18. Each cutting wire 18 can have a plurality of blades 20 clustered at or near the midpoint of the cutting wire.

Each cutting wire 18 can be formed from spring wire. The material used to create the wire 18 can be a metal, metal alloy, polymer, or the like. For example, in some embodiments, the spring wire can be spring steel. In some other embodiments, the spring wire can be a shape memory alloy such as Nitinol. As illustrated, each cutting wire 18 is largely circular in cross-section. Each cutting wire 18 can have other geometries. A cutting wire 18 can be flattened, with an oval cross-section. A cutting wire 18 can be square or rectangular or triangular, or other multisized geometries, in cross-section. A cutting wire 18 with a non-circular cross-section may have advantages in performance or manufacturing. Alternatively, a cutting wire 18 with a circular cross-section may have performance advantages.

As can be seen in the Figures, the length of the cutting wires 18 defines the length of the cutting unit 12 as the cutting wire 18 length defines the maximum distance between the first securement member 14 and the second securement member 16. The cutting unit 12 can be formed in a variety of different diameters and different lengths, in order to accommodate individual differences in vasculature and a wide variety of differences in possible lesions. In some embodiments, the cutting wires 18 can be in the range of about 3 to 25 millimeters long. An exemplary cutting wire 18 can be in the range of about 4 to 15 millimeters long.

Each cutting wire 18 has a first end 22 and a second end 24. The first end 22 is secured to the first securement member 14 and the second end 24 is secured to the second securement member 16. Each cutting wire 18 can be considered as having a distal end 22 and a proximal end 24. The distal end 22 is secured to the distal securement member 14 and the proximal end 24 is secured to the proximal securement member 16.

The securement members 14 and 16 shown in this embodiment are annular ring-like structures to which the cutting wires 18 are attached or connected. It should be understood, however, that the securement members 14 and 16 in other embodiments can take other shapes or forms. For example, the securement members 14 and 16 can be ovals, triangles, squares or other multi-sized shapes, or can include structures such as discs, caps, and the like.

As noted, each of the cutting wires 18 can be formed from a metallic alloy such as Nitinol or other suitable material. The cutting wires 18 can be attached to the securement members 14, 16 using appropriate attachment techniques. Some examples of attachment techniques include soldering, brazing, adhesion attachment, mechanical interlocking or attachment, thermal bonding such as sonic or laser welding or RF.

Alternatively, the cutting wires 18 can be integrally formed with one or more of the securement members 14 and

16. In some embodiments, the cutting wires 18 and one of the first securement member 14 or the second securement member 16 can be laser cut from a single metal blank. In some embodiments, the cutting wires 18, the first securement member 14 and the second securement member 16 can be laser cut from a metal blank. In some embodiments, a laser cutting process similar to that used in forming stents can be used.

In the embodiment shown, the first or distal securement member 14 provides an anchor point for the first or distal ends 22 of the cutting wires 18. The first or distal securement member 14 also provides an anchor point for an end 38 of an activation wire 26. Axial movement of the activation wire 26 causes corresponding axial movement of the first or distal securement member 14. Pulling on the activation wire 26 causes the first or distal securement member 14 to move towards the second or proximal securement member 16, thereby causing the cutting wires 18 to deflect outward.

While not illustrated, the end 38 of the activation wire 26 can alternatively be attached to the second or proximal securement member 16. In this instance, the proximal securement member 16 can slide, and the activation wire 26 could be pushed in order to move the second or proximal securement member 16 towards the first or distal securement member 14, thereby causing the cutting wires 18 to deflect outward.

The second or proximal securement member 16 provides an anchor point for the second or proximal ends 24 of the cutting wires 18. The second or proximal securement member 16 can be stationary, as illustrated for example in FIGS. 1, 3 and 4. The second or proximal securement member 16 can be moveable, as illustrated for example in FIGS. 5, 6 and 7.

The cutting unit 12 can include a stop 28 that is configured to limit how close the first or distal securement member 14 can move towards the second or proximal securement member 16. The stop 28 can be formed integrally with either the first or distal securement member 14 or the second or proximal securement member 16, or the stop 28 can be formed separately and then secured to one of the securement members 14, 16. As illustrated, the stop 28 has been formed integrally with the first or distal securement member 14. In some embodiments, the stop 28 and the first or distal securement member 14 can be laser cut from a single metal or metallic blank. In some embodiments, the stop 28, the cutting wires 18 and at least the first or distal securement member 14 can be integrally formed via laser cutting.

While not illustrated, an end of the stop 28 can interact with structure present on the second or proximal securement member 16 to prevent relative radial movement between the first or distal securement member 14 and the second or proximal securement member 16, if the stop is formed integrally with the first or distal securement member 14. Alternatively, one or more of the first or distal securement member 14 or the second or proximal securement member 16 can include structure that interacts with the housing 30 to prevent radial movement. For example, a securement member 14 or 16 can include a groove that interacts with a corresponding protrusion within the housing 30, or the securement member 14 or 16 can include a protrusion that interacts with a corresponding groove within the housing 30.

Each of the first or distal securement member 14 and the second or proximal securement member 16 can be formed having various geometries. The first or distal securement member 14 can be cylindrical in shape. The second or proximal securement member 16 can be cylindrical in shape. Each securement member 14, 16 can be formed from a metallic material. Some examples of suitable metals and metal alloys include stainless steel, such as 304v stainless steel or 316L stainless steel; nickel-titanium alloys such as super elastic or linear elastic nitinol, nickel-chromium alloy, nickel-chromium-iron alloy, cobalt alloy, or the like; or other suitable material.

While the size of the intravascular cutting device can vary, in some embodiments, each of the first or distal securement member 14 and the second or proximal securement member 16 can be in the range of about 1 to 3 millimeters in diameter and in the range of about 0.5 to 3 millimeters in length.

Portions of the intravascular cutting device may also be made of, include, doped with, include a layer of, or otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location.

For example, each securement member 14, 16 can include or be formed from a radiopaque material. Suitable materials can include, but are not limited to, bismuth subcarbonate, iodine, gold, platinum, palladium, tantalum, tungsten or tungsten alloy, and the like.

Once the first or distal end 22 and the second or proximal end 24 of a cutting wire 18 have been secured to or formed integrally with the first or distal securement member 14 and the second or proximal securement member 16, respectively, the cutting wire 18 can be considered to have a free length that is equal to the length of the cutting wire 18 minus the portions at either end 22, 24 that are secured to or formed with the securement members 14, 16. The free length can be considered to be the distance between the securement members 14, 16 when the cutting wires 18 are generally straight.

In the first or non-cutting configuration, the first securement member 14 and the second securement member 16 are positioned apart a distance approximately equal to the free length of the cutting wire 18. In the second or cutting configuration, the first securement member 14 and the second securement member 16 are positioned apart a distance that is less than the free length of the cutting wire.

Figure 1:
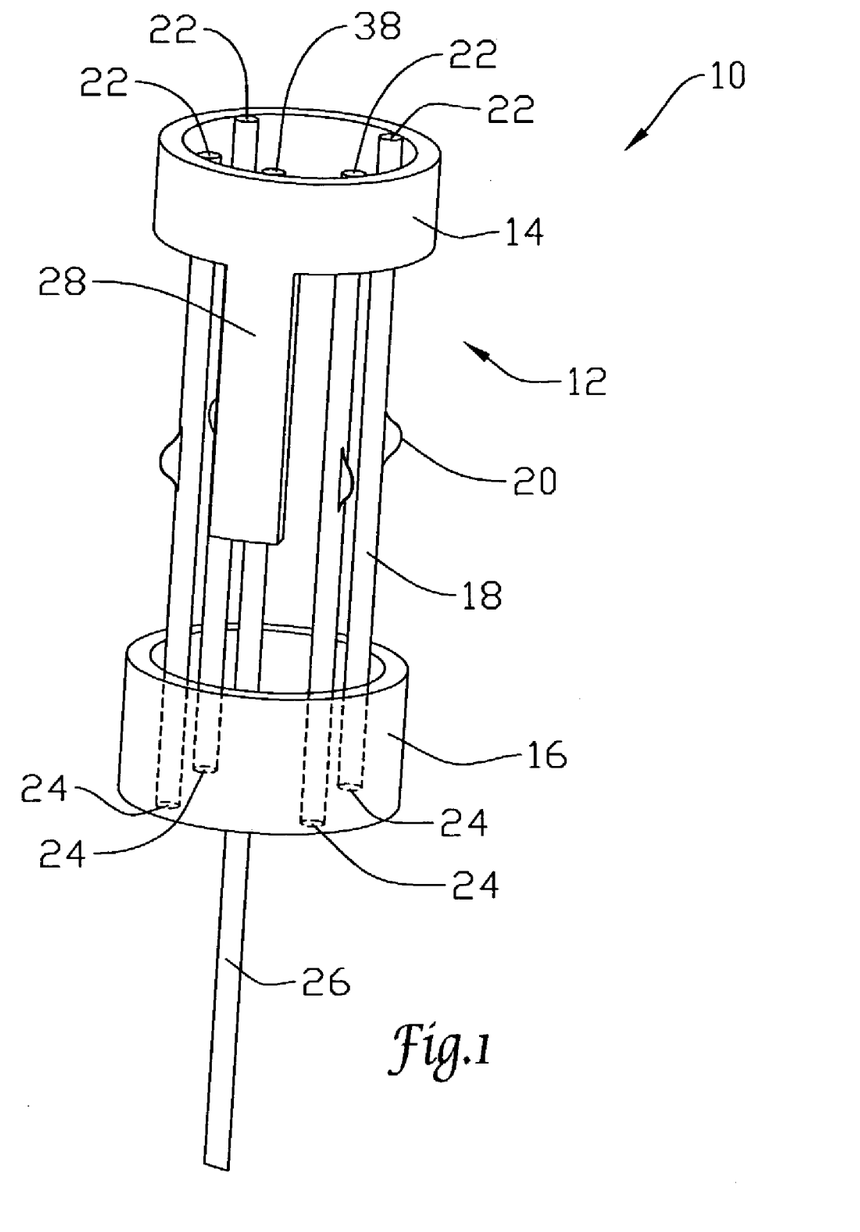
FIG. 1 is a perspective view of an intravascular cutting device in accordance with an embodiment of the present invention, shown without a housing and in a non-cutting position.

In this embodiment, because the cutting wires 18 are formed from spring wire, the cutting wires 18 can be used to bias the cutting unit 12 into the first or non-cutting configuration, as illustrated for example in FIG. 1. In other embodiments, other biasing mechanisms such as springs can be used. In this configuration, the blades 20 are effectively retracted, and cannot cut tissue. If the cutting wires 18 are compressed by moving the first or distal securement member 14 towards the second or proximal securement member 16, the cutting wires 18 can bend. When the compressive force is removed, the cutting wires 18 can straighten out and will once again bias the cutting unit 12 into the first or non-cutting configuration.

Figure 3:
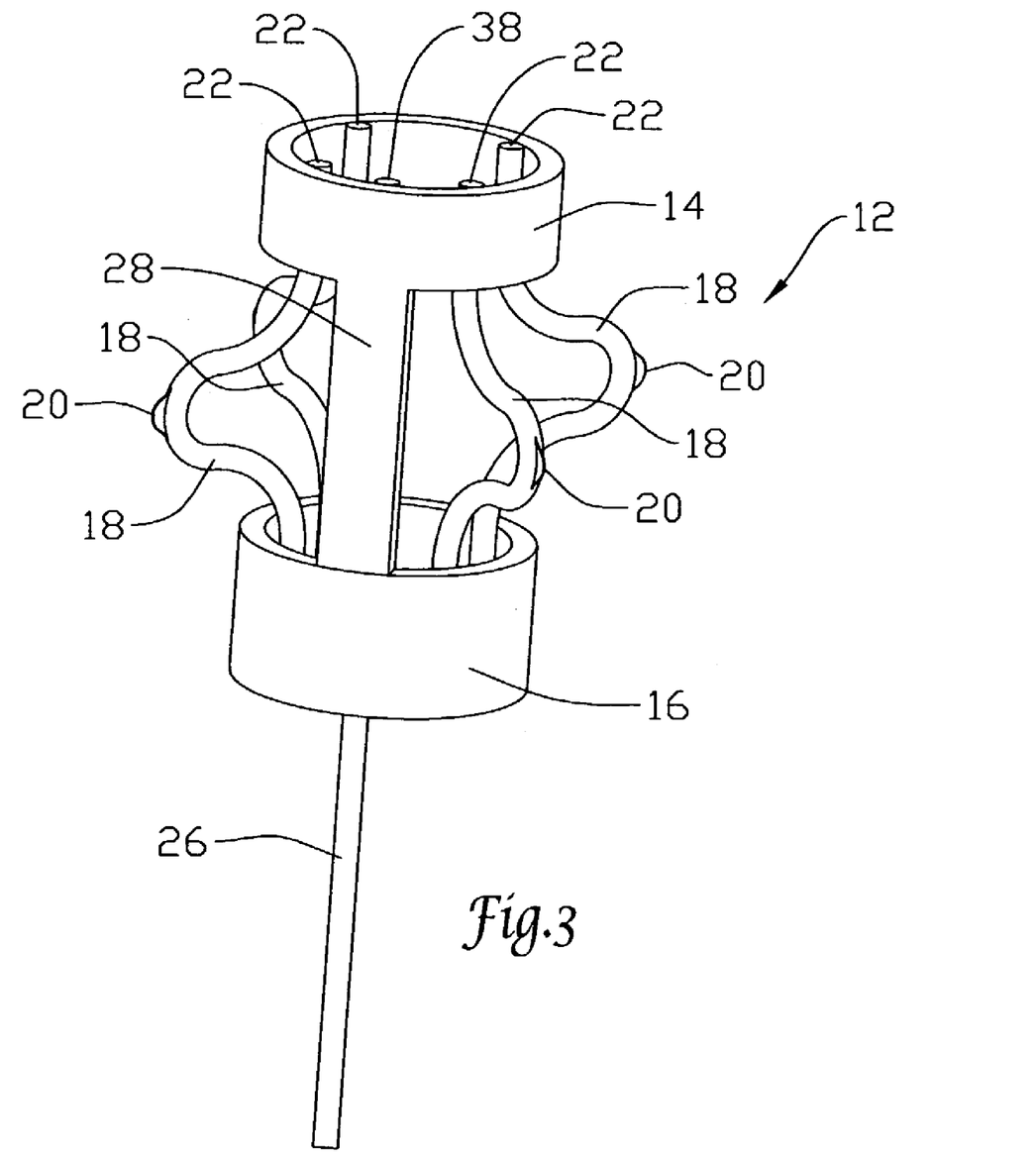
FIG. 3 is a perspective view of the intravascular cutting device of FIG. 1, shown in a cutting position.

FIG. 3 illustrates the cutting unit 12 in a second, or cutting configuration. In this configuration, the first or distal securement member 14 has been moved axially towards the second or proximal securement member 16. As a result, the cutting wires 18 are forced to bend or deflect. The cutting wires 18 can be predisposed to bend or deflect in an outward direction, as illustrated. As the cutting wires 18 bend outward, the blade attached to each cutting wire 18 also moves outward into a cutting position.

Figure 2:
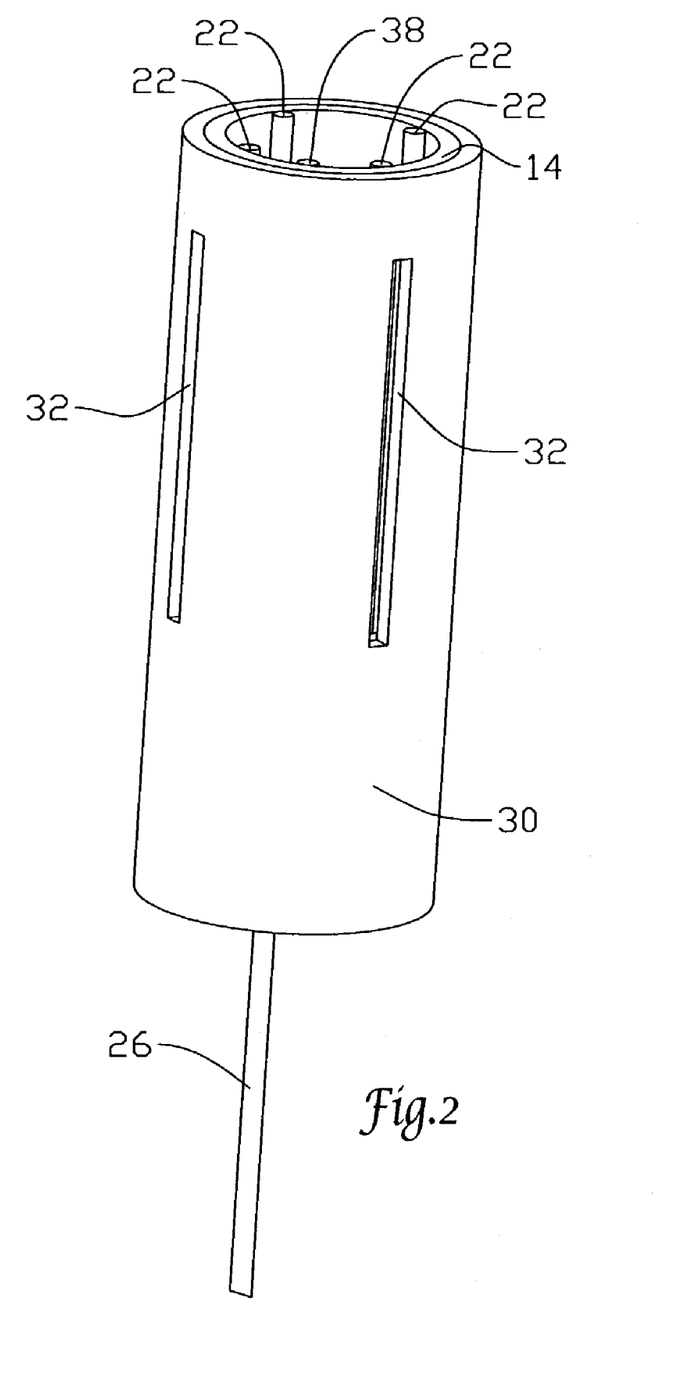
FIG. 2 is a perspective view of the intravascular cutting device of FIG. 1, shown positioned within a housing in a non-cutting position.

The cutting unit 12 can be positioned within a housing 30. A suitable housing 30 is illustrated in FIG. 2 as a cylindrical tube. The housing 30 can be made of any suitable material, for example, a polymeric material, a metal, a metal alloy, a metal-polymer composite, or the like. The housing 30 can include one or more longitudinal slots 32 that are configured to align with each of the one or more cutting wires 18. For example, if the cutting unit 12 has four equally spaced cutting wires 18, the housing 30 can have four equally spaced longitudinal slots 32.

In some embodiments, each of the longitudinal slots 32 can be dimensioned to accommodate the particular cutting wire 18 and diamond blade 20 present thereon. Each longitudinal slot 32 can be in the range of about 4 to 29 millimeters long and in the range of about 0.01 to 1 millimeter in width. In some embodiments, the longitudinal slots 32 can be even smaller or can even be absent, as in some embodiments the cutting wires 18 and diamond blades 20 can cut through and penetrate the housing 30 if the housing 30 is formed of a sufficiently soft polymeric material.

The housing 30 itself can be formed from a variety of polymeric materials. Examples of suitable polymers include polyurethane, a polyether-ester such as ARNITEL® available from DSM Engineering Plastics, a polyester such as HYTREL® available from DuPont, a linear low density polyethylene such as REXELL®), a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials.

In some embodiments, the housing 30 can have an overall length in the range of about 1 to 32 millimeters and a diameter in the range of about 1.01 to 3.5 millimeters. In some embodiments, the housing 30 can represent a catheter structure such as a guide catheter and in such embodiments can be substantially longer than those illustrated. For example, if the housing 30 is a guide catheter it can be in the range of about 100 to 150 centimeters in length.

In some embodiments, the housing 30 can have an inner diameter that is configured to accommodate the cutting unit 12 and an outer diameter that is configured to fit within a particular vascular lumen. In some embodiments, the housing 30 can have an outer diameter that permits blood flow between an exterior of the housing 30 and the vascular lumen. In some embodiments, the housing 30 can include ports or openings (not illustrated) that permit blood to reach the interior of the housing 30. Such ports or openings can be placed in the housing 30 such that they are at or near the a proximal end of the housing 30. As a result, blood can pass through the interior of the housing 30 and thereby permit continued blood flow past a vascular lesion.

The housing 30 can also be formed from a variety of metallic materials as well. Examples of suitable metallic materials include stainless steels (e.g. 304v stainless steel), nickel-titanium alloys (e.g., nitinol such as super elastic or linear elastic nitinol), nickel-chromium alloys, nickel-chromium-iron alloys, cobalt alloys, nickel, titanium, platinum, or alternatively, a polymer material, such as a high performance polymer, or other suitable materials, and the like.

Figure 4:
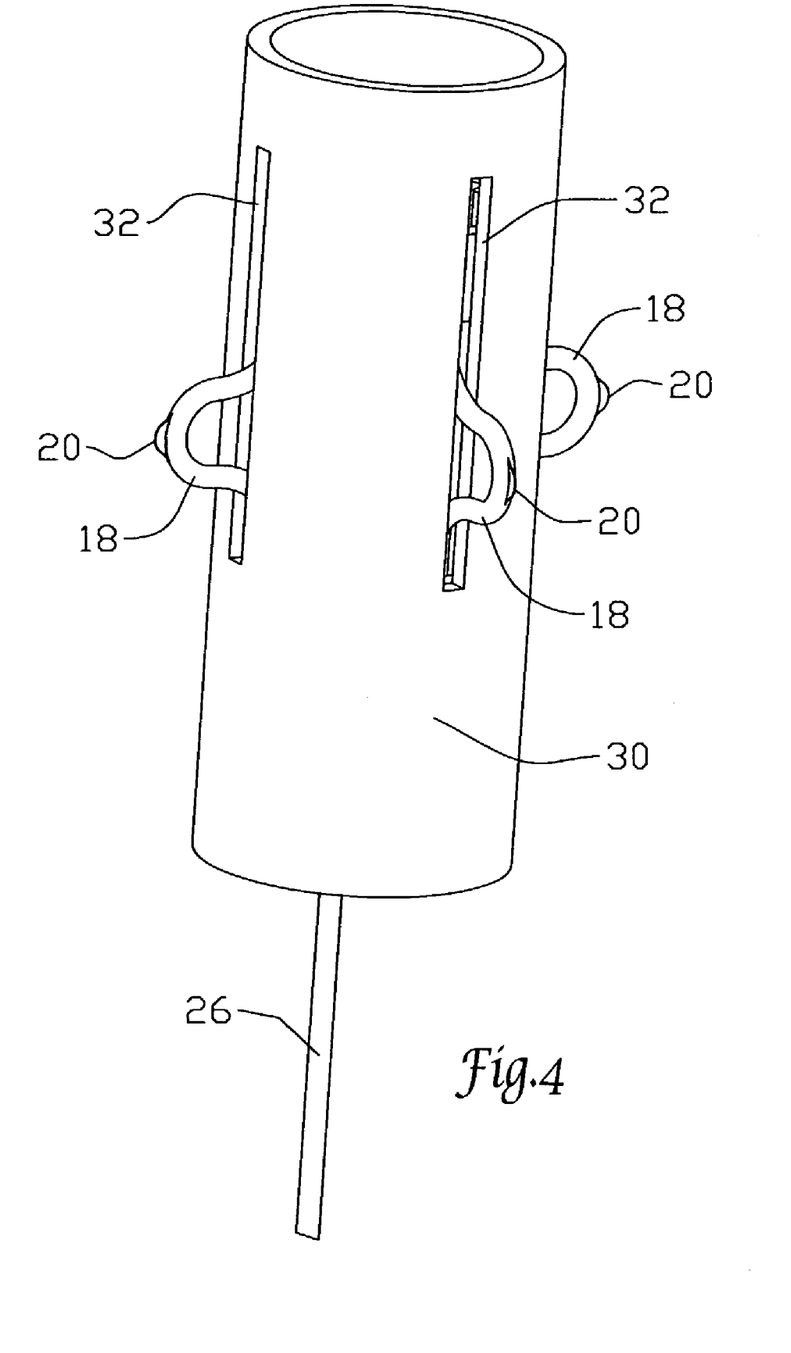
FIG. 4 is a perspective view of the intravascular cutting device of FIG. 3, shown positioned within the housing of FIG. 2.

FIG. 4 illustrates the cutting unit 12 in its second or cutting configuration, within the housing 30. In this configuration, each of the cutting wires 18 can bend or deflect outward sufficiently to expose each of the diamond blades 20. The diamond blades 20 can be retracted within the housing 30 when the cutting unit 12 is in its first or non-cutting configuration, as seen for example in FIG. 2.

As noted, the cutting unit 12 can be moved from its first or non-cutting configuration to its second or cutting configuration by applying a force on the activation wire 26. The activation wire 26 can have a variety of geometries and can be made from a variety of materials such as metals, metal alloys, and polymers, as discussed above. An exemplary activation wire 26 is circular in cross-section and is formed from a metallic material having sufficient strength and resistance to stretching. One example of a suitable material is stainless steel. When the pulling force is removed from the activation wire 26, the cutting wires 18 can return the cutting unit 12 to its first or non-cutting configuration.

Figure 5:
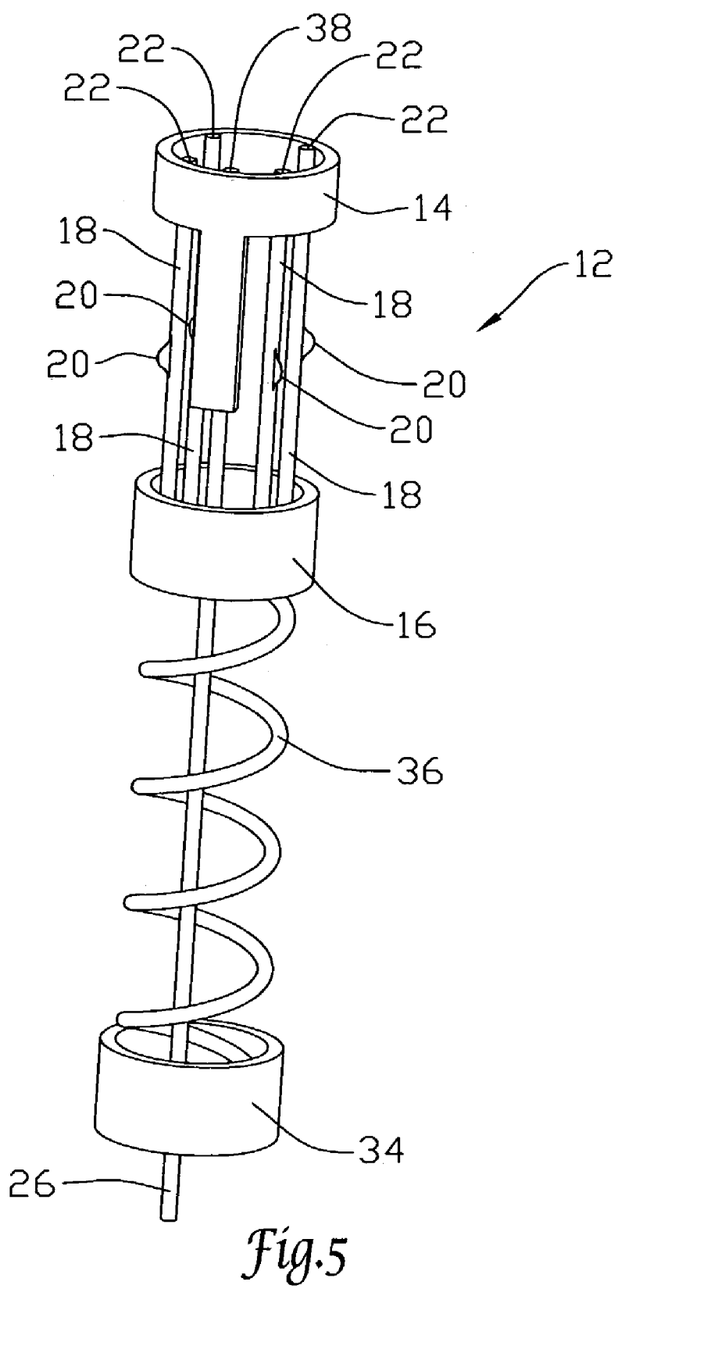
FIG. 5 is a perspective view of an intravascular cutting device in accordance with another embodiment of the present invention, shown without a housing in a non-cutting position.
Figure 6:
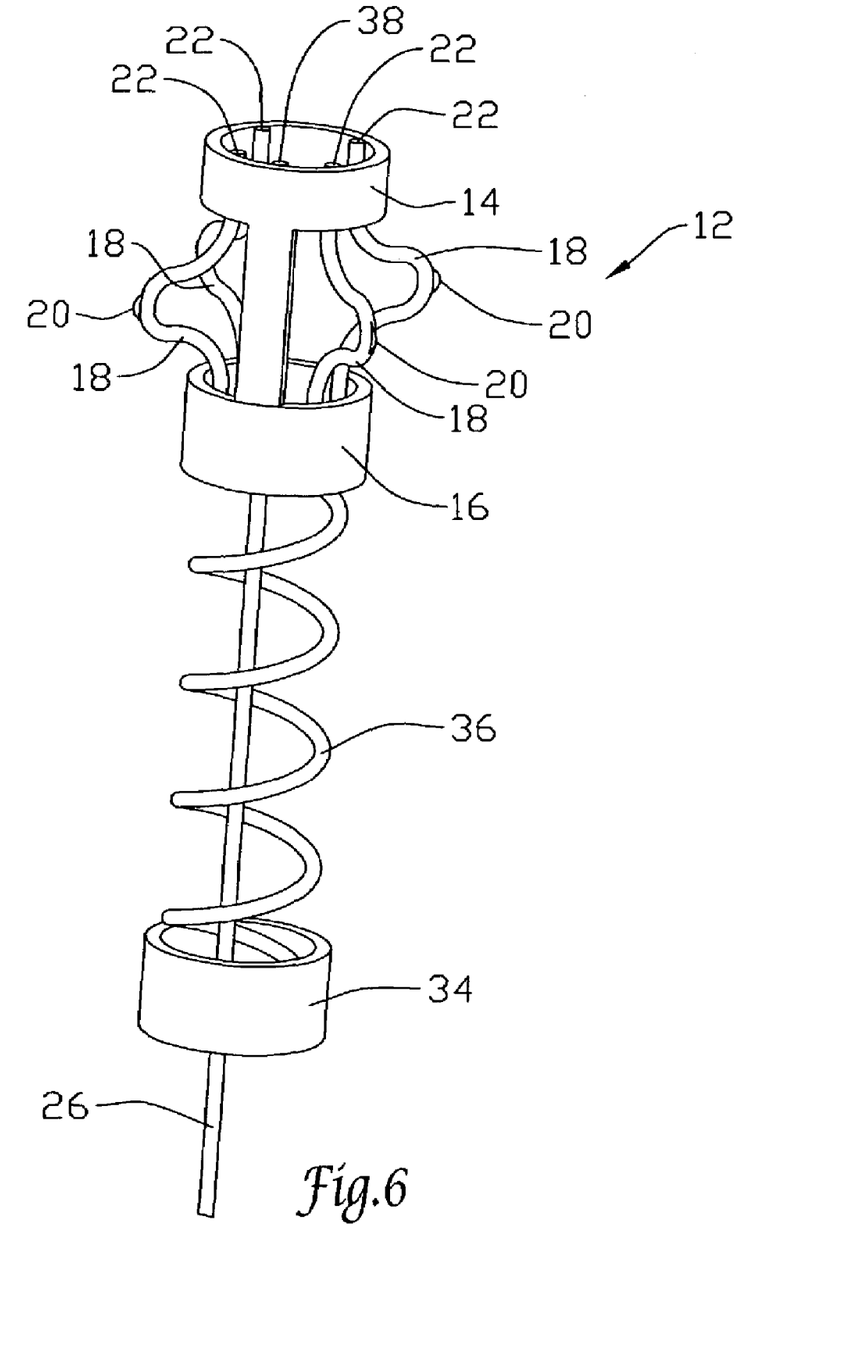
FIG. 6 is a perspective view of the intravascular cutting device of FIG. 5, shown without a housing in a cutting position.
Figure 7:
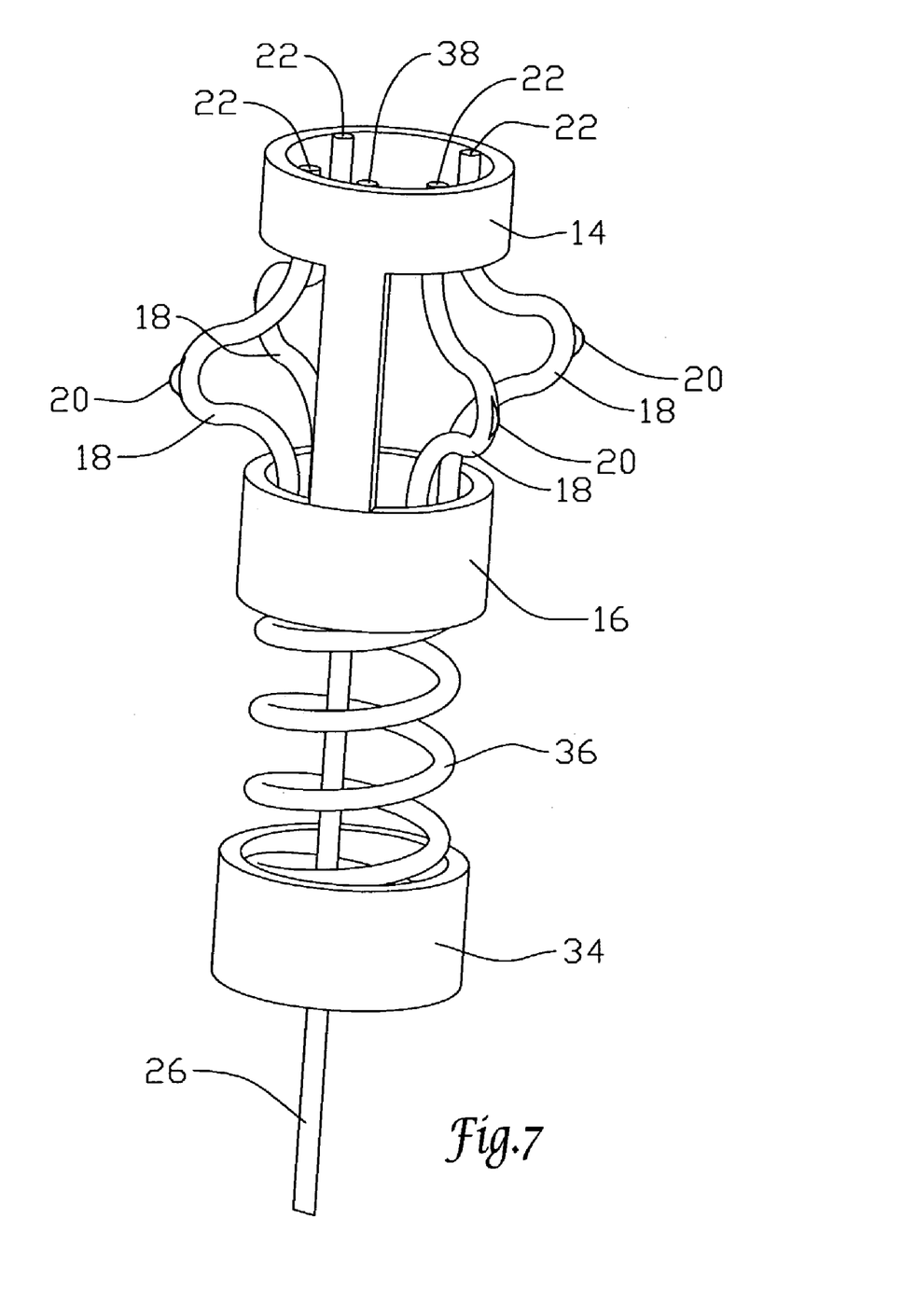
FIG. 7 is a perspective view of the intravascular cutting device of FIG. 5, shown without a housing in another cutting position.

FIGS. 5, 6 and 7 illustrate a particular embodiment of the intravascular cutting device 10. As discussed with respect to the earlier Figures, the intravascular cutting device 10 includes a cutting unit 12 that has a first or distal securement member 14, a second or proximal securement member 16 and one or more cutting wires 18 secured between the first or distal securement member 14 and the second or proximal securement member 16. A stop 28 limits a minimum distance between the first or distal securement member 14 and the second or proximal securement member 16. An activation wire 26 is secured to the first or distal securement member 14.

This embodiment adds several features. Notably, this embodiment includes a third or positioning securement member 34 and biasing means that bias the cutting unit 12 in a particular position with respect to the third or positioning securement member 34. FIG. 5 shows the cutting unit 12 in a non-cutting configuration. FIG. 6 shows the cutting unit 12 in a first cutting configuration while FIG. 7 illustrates a second cutting configuration.

The third or positioning securement member 34 can be formed having various geometries. The third or positioning securement member 34 can be cylindrical in shape and can be formed from a metallic material. The third or positioning securement member 34 can include or be formed from either tantalum or platinum, which can make the securement member 34 more visible to X-ray. While the size of the intravascular cutting device 10 can vary, the third or positioning securement member 34 can be in the range of about 1 to 3 millimeters diameter and in the range of about 0.5 to 3 millimeters in length. The third or positioning securement member 34 can be secured to the inside of the housing 30.

The biasing means can be attached at one end to the cutting unit 12 and at the other end to the third or positioning securement member 34. The biasing means can be formed from any material that will bias the cutting unit 12 into a position away from the third or positioning securement member 34. The biasing means can be a rubber material. An exemplary biasing means can be a metal spring member 36 that has a relaxed length that positions the cutting unit 12 as illustrated in FIGS. 5 and 6. The spring member 36 would be compressed as the cutting unit 12 moves into the second cutting configuration as illustrated in FIG. 7.

In use, the intravascular cutting device 10 as illustrated in FIGS. 5, 6 and 7 would be positioned proximate a lesion in a patient's vasculature. The intravascular cutting device 10 can be placed proximate the lesion by passing the intravascular cutting device 10 over a previously positioned guidewire. A guide catheter can also be used to place the intravascular cutting device 10.

As illustrated herein, the intravascular cutting device 10 is in a non-cutting configuration (see FIG. 5) as it is placed proximate the patient's lesion. In some embodiments, a physician or other professional can provide a pulling force on the activation wire 26, to cause the first or distal securement member 14 to move towards the second or proximal securement member 16, thereby causing the cutting unit 12 to move into a cutting configuration, as illustrated for example in FIG. 6. The intravascular cutting device 10 can be rotated to excise the lesion.

The first or distal securement member 14 will move towards the second or proximal securement member 16 until travel is limited by the stop 28. If the physician or other professional continues to provide a pulling force on the activation wire 26, the cutting unit 12 itself will move within the housing (not illustrated) towards the third or positioning securement member, as illustrated for example in FIG. 7. If the activation wire 26 is pulled a particular distance after the cutting unit 12 has hit the stop 28, the diamond blades 20 secured to the cutting wires 18 will axially travel that same distance. Thus, the physician or other professional is provided with means of controlling the length of any cut made.

It should be understood that although the above discussion was focused on a cutting device and methods of use within the vascular system of a patient, other embodiments of cutting devices or methods in accordance with the invention can be adapted and configured for use in other parts of the anatomy of a patient. For example, devices and methods in accordance with the invention can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

I claim:

1. An intravascular cutting device comprising:
   (a) a housing having a longitudinal slot;
   (b) a cutting unit comprising:
      (i) a distal securement member;
      (ii) a proximal securement member; and
      (iii) a cutting wire having a distal end and a proximal end, the distal end of the cutting wire attached to the distal securement member, the proximal end of the cutting wire attached to the proximal securement member;
   (c) an activation wire attached to the distal securement member;
   (d) a positioning securement member secured to the housing, the positioning securement member located proximal of the cutting unit; and
   (e) a biasing member having a distal end and a proximal end, the distal end of the biasing member attached to the proximal securement member of the cutting unit, the proximal end of the biasing member attached to the positioning securement member;
   wherein the cutting unit is biased to a non-cutting configuration.

2. The intravascular cutting device of claim 1, wherein pulling on the activation wire forces the distal securement member to move towards the proximal securement member, thereby causing the cutting unit to assume a cutting position in which a portion of the cutting wire extends through the longitudinal slot and exterior of the housing.

3. The intravascular cutting device of claim 2, wherein the cutting unit further comprises a stop that limits a minimum distance between the distal securement member and the proximal securement member, whereby pulling the activation wire beyond a point at which the stop has limited relative travel between the distal securement member and the proximal securement member causes the cutting unit to move towards the positioning securement member.

4. The intravascular cutting device of claim 3, wherein the cutting wire will axially cut a distance equal to travel of the activation wire beyond the point at which the stop has limited relative travel between the distal securement member and the proximal securement member.

5. The intravascular cutting device of claim 1, wherein the cutting wire comprises a spring wire bearing a diamond blade.

6. The intravascular cutting device of claim 5, wherein the spring wire comprises either stainless steel or a nickel titanium alloy.

7. The intravascular cutting device of claim 1, wherein the housing comprises a tube.

8. The intravascular cutting device of claim 1, wherein the distal securement member, the proximal securement member and the positioning securement member each comprise a radiopaque material.

9. A method of excising a lesion within a vascular system, the method comprising;
   (a) positioning an intravascular cutting device proximate the lesion, the intravascular cutting device comprising:
      (i) a first securement member;
      (ii) a second securement member spaced from the first securement member;
      (iii) a cutting wire having a first end and a second end, the first end of the cutting wire attached to the first securement member and the second end of the cutting wire attached to the second securement member, the cutting wire biased to a non-cutting position;
      (iv) an activation wire attached to the first securement member;
      (v) a housing having a longitudinal slot, wherein the first securement member, the second securement member and the cutting wire together form a cutting unit having a first configuration in which the cutting wire remains within the housing and a second configuration in which a portion of the cutting wire extends through the longitudinal slot and outside of the housing; and
      (vi) the cutting unit further comprising a stop that limits a minimum distance between the first securement member and the second securement member, whereby pulling the activation wire beyond a point at which the stop has limited relative travel between the first securement member and the second securement member causes the cutting unit to move within the housing;
   (b) manipulating the activation wire to move the first securement member towards the second securement member in order to move the cutting wire into a cutting position; and
   (c) cutting the lesion.

10. The method of claim 9, wherein the cutting wire will axially cut a distance equal to travel of the activation wire beyond the point at which the stop has limited relative travel between the first securement member and the second securement member.

* * * * *